US011513121B2

(12) United States Patent
Frostell et al.

(10) Patent No.: US 11,513,121 B2
(45) Date of Patent: Nov. 29, 2022

(54) METHOD FOR VIRUS ASSAY

(71) Applicant: GE Healthcare Bio-Sciences AB, Uppsala (SE)

(72) Inventors: Asa Frostell, Uppsal (SE); Elisabeth Wallby, Uppsala (SE); Asa Hagner-McWhirter, Uppsala (SE); Linnea Nygren Babol, Uppsala (SE)

(73) Assignee: CYTIVA SWEDEN AB, Uppsala (SE)

( * ) Notice: Subject to any disclaimer, the term of this patent is extended or adjusted under 35 U.S.C. 154(b) by 158 days.

(21) Appl. No.: 16/762,586

(22) PCT Filed: Nov. 8, 2018

(86) PCT No.: PCT/EP2018/080569
§ 371 (c)(1),
(2) Date: May 8, 2020

(87) PCT Pub. No.: WO2019/092082
PCT Pub. Date: May 16, 2019

(65) Prior Publication Data
US 2020/0264175 A1 Aug. 20, 2020

(30) Foreign Application Priority Data

Nov. 10, 2017 (GB) .................................... 1718579
Mar. 29, 2018 (GB) .................................... 1805178

(51) Int. Cl.
| G01N 33/68 | (2006.01) |
| A61K 31/37 | (2006.01) |
| A61K 31/4365 | (2006.01) |
| A61K 31/4439 | (2006.01) |
| A61K 31/616 | (2006.01) |
| G01N 33/569 | (2006.01) |
| C12N 7/00 | (2006.01) |
| G01N 33/543 | (2006.01) |

(52) U.S. Cl.
CPC ......... G01N 33/56983 (2013.01); C12N 7/00 (2013.01); G01N 33/54373 (2013.01); *C12N 2710/10051* (2013.01); *G01N 2333/075* (2013.01)

(58) Field of Classification Search
CPC .. A61K 2300/00; A61K 31/555; A61K 33/26; A61K 38/193; A61P 43/00
See application file for complete search history.

(56) References Cited

U.S. PATENT DOCUMENTS

2006/0223053 A1\* 10/2006 Roper .............. G01N 33/54373
435/7.1
2006/0233053 A1 10/2006 Roper

FOREIGN PATENT DOCUMENTS

WO 98/41618 A1 9/1998

OTHER PUBLICATIONS

Waddington Simon N et al: "Adenovirus serotype 5 hexon mediates liver gene transfer", Cell, Cell Press, Amsterdam, NL, vol. 132 (3), 2008:397-409.\*
PCT International Search Report and Written Opinion for PCT Application No. PCT/EP2018/080569 dated Dec. 20, 2018 (11 pages).
Great Britain Search Report for GB Application No. 1718579.4 dated Jul. 20, 2018 (5 pages).
Kalyuzhniy et al., "Adenovirus Serotype 5 Hexon is Critical for Virus Infection of Hepatocytes in vivo," PNAS, 2008, 105(14):5483-5488.
Karlsson, "Biosensor Binding Data and its Applicability to the Determination of Active Concentration," Biohys Rev, 2006 (12 pages).
Lortat-Jacob et al., "Kinetic Analysis of Adenovirus Fiber Binding to its Receptor-Reveals an Avidity Mechanism for Trimeric Receptor-Ligand Interactions," The Journal of Biological Chemistry, 2001, 276(12):9009-9015.
Parker et al., "Multiple Vitamin K-Dependent Coagulation Zymogens Promote Adenovirus-Mediated Gene Delivery to Hepatocytes," Blood, 2006, 108(8):2554-2561.
Waddington et al., "Adenovirus Serotype 5 Hexon Mediates Liver Gene Transfer," Cell, 2008, 132:397-409.

\* cited by examiner

*Primary Examiner* — Barry A Chestnut
(74) *Attorney, Agent, or Firm* — Eversheds Sutherland (US) LLP

(57) ABSTRACT

The present invention relates to a method for virus assay. More closely the invention relates a method for total quantification of adenovirus in a sample as well as total and functional (active) adenovirus in a sample. The method for determining adenovirus concentration in a sample comprises subjecting said sample to SPR (surface plasmon resonance) assay with immobilized FX (Factor X) and/or immobilized CAR (coxsackievirus and adenovirus receptor) on a sensor surface, wherein the adenovirus concentration is determined from sample binding to immobilized FX and/or immobilized CAR. CAR can be replaced by an ligand binding to adenovirus fiber, such as an anti-adenovirus fiber antibody. FX can be replaced by a ligand binding to adenovirus hexon, such as an anti-adenovirus hexon antibody. The method can be used for quality control in an adenovirus purification process, for example for gene therapy.

14 Claims, 9 Drawing Sheets

Fig 6

ATCC standard binding to FX (x 10⁸ virus particles/ml)
29
14.5
7.25
3.63
1.81
0.9

METHOD FOR VIRUS ASSAY

CROSS REFERENCE TO RELATED APPLICATIONS

This application claims the priority benefit of PCT/EP2018/080569 filed on Nov. 8, 2018, which claims priority benefit of Great Britain Patent Application Nos. 1718579A and 1805178.9 filed Nov. 10, 2017 and Mar. 29, 2018, respectively, the entire contents of which are hereby incorporated by reference herein.

FIELD OF THE INVENTION

The present invention relates to a method for virus assay. More closely the invention relates a method for total quantification of adenovirus in a sample as well as as well as total and functional (active) adenovirus in a sample.

BACKGROUND OF THE INVENTION

Human adenoviruses have been classified into six species (A to F) with 55 known serotypes causing a wide range of illnesses, from mild respiratory infections in young children (known as the common cold) to life-threatening multi-organ disease in people with a weakened immune system.

Adenoviruses are common pathogens that are widely used experimentally and in completed and ongoing clinical trials for gene delivery in oncology, cardioangiology, and regenerative medicine and as vaccine vectors.

Kalyuzhniy et al. PNAS, 2008, 105, 5483-5488, describes the $Ca^{2+}$ dependent mechanism of FX binding to the Ad5 hexon trimer, using SPR (surface plasmon resonance) technology. They did this study through immobilization of Ad5 to a sensor chip and injection of FX (Factor X) whereby binding kinetics and binding specificity could be studied. There are no descriptions of FX being immobilized and virus injected, nor do the authors in any way study or discuss quantification of virus particles.

Parker et al, describes in Blood, October 2006, Volume 108, No 8 in FIG. 5C, SPR with immobilized FX and injections of different concentrations of adenovirus. They demonstrate a dose response relationship but do not take this further nor do they discuss this as a possibility to quantify the adenovirus content of unknown samples.

Common techniques used for Ad5 total virus particle titer quantification are qPCR and HPLC based methods. SDS PAGE and Western blot can be used for characterization but also quantitation. NanoSigth (Malvern) is an instrument for quantification of particle concentration and particle size distribution that is based on laser illumination the sample and utilizes nanoparticle tracking analysis (NTA). They all have different limitations that need to be considered. Apart from NTA and the HPLC methods they are all rather time-consuming methods. The qPCR is based on hexon DNA quantitation and requires DNA preparation before analysis. Any free DNA in the sample as well as variation in the sample preparation introduce variation and can affect the results. The NTA analysis is unspecific and only based on particle size. Any free virus proteins in the sample can introduce inaccurate results for the SDS-PAGE and Western blot analysis.

For analysis of infectious virus particle titer, cell based assays such as TCID50 or similar assays using microscopy of cells, which are subjected to virus infection. The cells are seeded at the same density and different dilutions of a virus sample is added. After incubation to allow the virus to infect the lowest dilution that will affect the cell morphology is determined and the infectious virus titer is calculated. These cell-based assays require at least one week to obtain the results and are also considered to be suffering from variation affected by the operator and protocols. Precision depends on the size of the dilution steps and often a visual estimation by the operator.

Thus, there is a need of better methods for quantification of total adenovirus as well as infectious virus which are more accurate as well as simpler to perform and less time consuming.

SUMMARY OF THE INVENTION

The present invention describes development of assays using standard curves as well as development of calibration free concentration assay (CFCA), aiming at estimating adenovirus concentration and ratios in samples.

In a first aspect, the invention relates to a method for determining adenovirus concentration in a sample, comprising subjecting said sample to SPR (surface plasmon resonance) assay with immobilized FX (Factor X) and/or immobilized CAR (coxsackievirus and adenovirus receptor) on a sensor surface, wherein the adenovirus concentration is determined from sample binding to immobilized FX and/or immobilized CAR. In this way the method may be used for both total quantification of adenovirus in a sample as well as functional (active) adenovirus in a sample.

In one embodiment, FX and said CAR are immobilized on different SPR surfaces or on the same SPR surface but on different regions or areas thereof. To obtain sample values from binding to both FX and CAR (from the same sample) is very valuable information for estimation of virus functionality.

In one embodiment, functional (or active, and sometimes also referred to as infectious) adenovirus is determined by binding to both FX and CAR by the same adenovirus.

In a preferred embodiment, FX or CAR is immobilized and the one of FX and CAR that is not immobilized is injected in a second step of the SPR assay for binding to relevant parts of the sample (adenovirus) already bound to the surface in a so called sandwich assay. In this way the intact, and therefore infectious, virus is captured. This embodiment is described further below in the Example section.

CAR may be replaced by an ligand binding to adenovirus fiber, such as an anti-adenovirus fiber antibody. FX may be replaced by a ligand binding to adenovirus hexon, such as an anti-adenovirus hexon antibody.

In one embodiment, the ratio between functional (active) adenovirus concentration and total adenovirus concentration is determined Preferably both FX and CAR are immobilized either on the same or different sensor surfaces (also called chips). It is very valuable to have these two concentration values as a guide in the purification of adenovirus from the production culture step to the final sterile filtration step as shown below in FIG. 2.

In one embodiment said FX and said CAR are immobilized on one SPR surface but on different regions or areas thereof. One flow channel associated with FX surface and one with CAR surface.

In another embodiment said FX and said CAR are immobilized on different SPR surfaces.

The result from the SPR assay(s) may be determined with standard curves as shown in Example 1 and 2 and 3 below.

The SPR assay(s) use in the method of the invention may also be CFCA (calibration free concentration analysis) assays as shown in Example 4 below.

In a second aspect the invention relates to use of the above method for quality control in one or more steps of an adenovirus purification process.

The method of the invention may also be used in a purification process of adenovirus for gene therapy. When the adenovirus is used for gene therapy a minimal infectious: total virus particle ratio of about 1/30 is required.

BRIEF DESCRIPTION OF THE DRAWINGS

FIG. 6 is an overlay plot of sensorgrams from different concentrations of adenovirus binding to immobilized FX;

DETAILED DESCRIPTION OF THE INVENTION

The present invention provides a method for simple and accurate calculation of total adenovirus concentration as well as concentration of infectious adenovirus particles. Furthermore, the invention provides a method for calculation of the ratio between the infectious virus particles and total virus particles in the same sample which in prior art had to rely on different methods (DNA quantitation and biological infectivity assay) performed at different times, which often introduced inaccuracy of the results.

The invention will now be described more closely in relation to some non-limiting Examples and the accompanying drawings.

Figure 1:
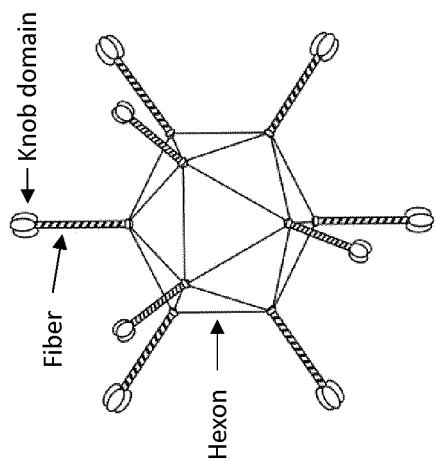
FIG. 1 is a schematic view of an adenovirus with arrows pointing at the hexagon, fiber and knob domain.

FIG. 1 is a schematic view of an adenovirus with arrows pointing at the hexon, fiber and knob domain.

Adenoviruses are principally made up of three major capsid proteins—hexon, penton, and fiber, FIG. 1. The crystal structures of Ad2 and Ad5 hexon have been solved and reveal a complex structure. The hexon, the major site of antigenicity in adenoviruses, is the most abundant capsid protein and is positioned at the virion surface, arranged into 240 homotrimeric structures interlinked from neighboring monomers, thus providing structural support. The fiber which engages the penton base at the capsid surface projects away from the virion, is highly variable in length, and is thought to be the major site determining cell infectivity.

For subgroup C adenoviruses, including Ad5, the globular fiber knob positioned at the end of the trimeric fiber shaft binds the coxsackievirus and adenovirus receptor (CAR), expressed in an anatomically similar manner in mice and humans.

Figure 2:
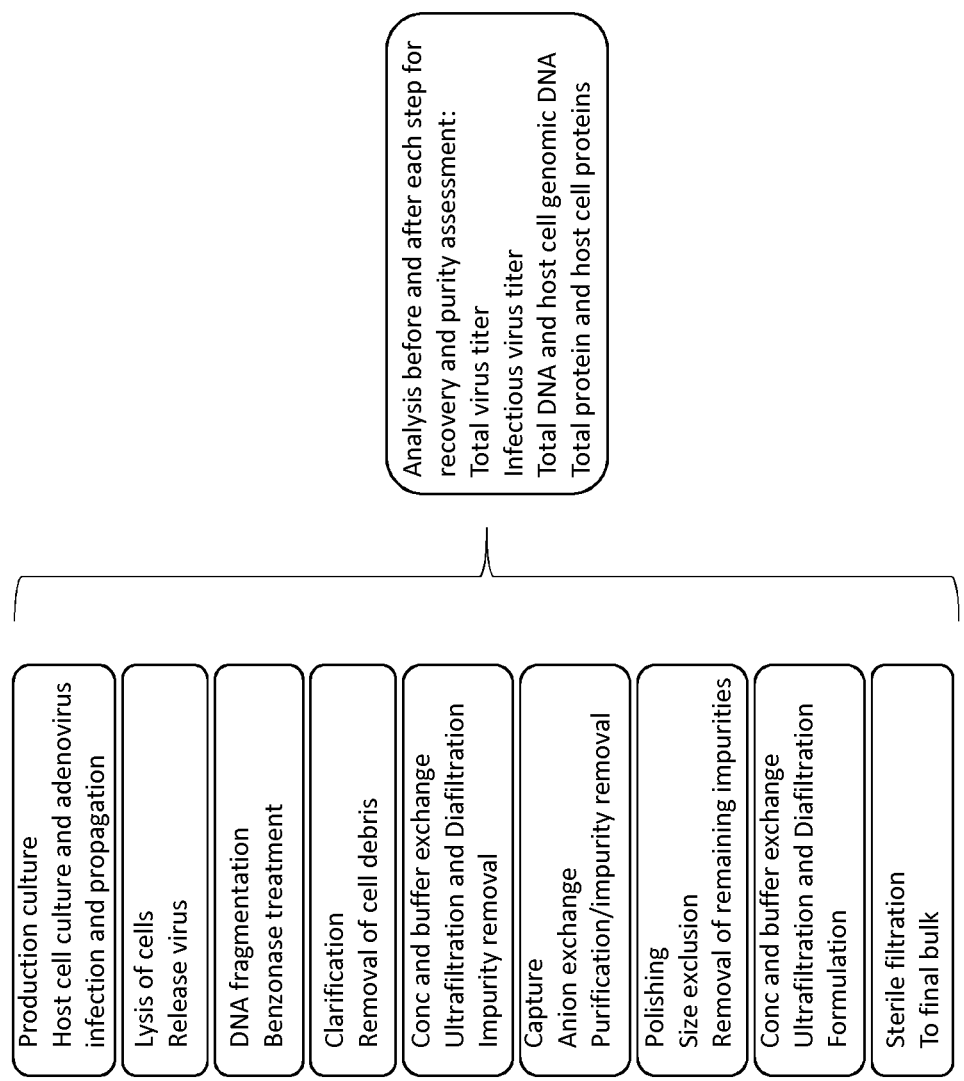
FIG. 2 is an overview the different steps in the procedure for adenovirus production.

FIG. 2 describes overview the different steps in the procedure for adenovirus production. Production culture, Host cell culture and adenovirus infection and propagation: HEK293.2sus cells were grown in CDM4HEK293 cell culture medium until 1×106 cells/mL were reached. The cells were then infected with E1/E3-deleted AdV5, coding for green fluorescent protein (GFP), with a multiplicity of infection of 10.

Lysis of Cells, Release Virus:

Time of harvest was 42 h post infection, and virus was released by detergent treatment using 0.5% Tween 20 for 4 h mixing at 37° C.

DNA Fragmentation, Benzonase Treatment:

At the same time as the lysis, 20 U/ml nuclease enzyme (Benzonase) was added together with MgCl2 to a final concentration of 2 mM.

Clarification, Removal of Cell Debris:

The harvest was subjected to normal flow filtration using ULTA 2 µm followed by 0.6 µm glass fiber filter.

Conc and Buffer Exchange, Ultrafiltration and Diafiltration, Impurity Removal:

Clarified harvest were subjected to tangential flow filtration using a hollow fiber filter with NMWC: Mr 300 000. The samples were concentrated 10 times and subjected to a 5-fold diafiltration into 20 mM Tris, pH 8+300 mM NaCl.

Capture, Anion Exchange Purification/Impurity Removal:

Capto Q ImpRes anion exchange resin with gradient elution.

Polishing, Size Exclusion, Removal of Remaining Impurities Capto core 700 multimodal resin was used. Capto Core 700 consists of an inert shell and a ligand-containing core, providing dual functionality to the resin. Pores in the shell allow small proteins and impurities to enter and be captured in the core, while the virus particles pass in the flowthrough.

Conc and Buffer Exchange, Ultrafiltration and Diafiltration, Formulation:

The Capto core 700 virus containing flowthrough was subjected to tangential flow filtration using a hollow fiber filter with NMWC: Mr 300 000. The samples were concentrated 5 times and subjected to a 5-fold diafiltration into 20 mM Tris, pH 8, 25 mM NaCl, 2 mM MgCl2 and 2.5% glycerol.

Sterile Filtration, to Final Bulk:

The final purified virus sample was filtered through a 0.2 µm polyethersulphone filter to obtain a sterile final bulk.

Analysis:

Total virus titer using qPCR for hexon DNA Infectious virus titer using a cell based assay and automated microscopy detecting GFP producing infected cells.

Figure 3:
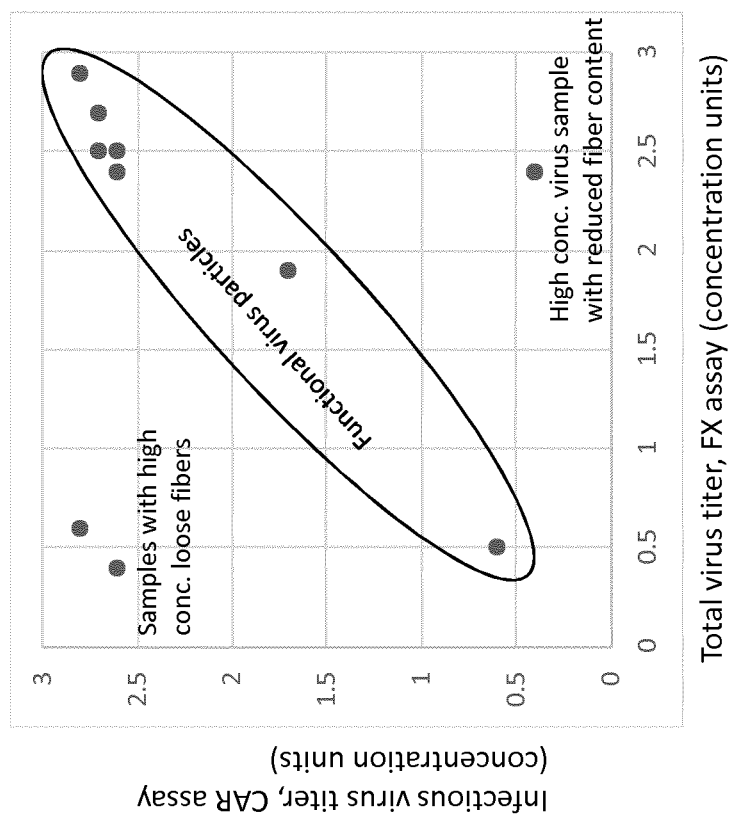
FIG. 3 shows a diagram of total adenovirus titer plotted against infectious adenovirus titer.

Total DNA and host cell genomic DNA using a PicoGreen assay and a qPCR for HEK293 GAPDH DNA Total protein and host cell proteins using the BCA assay and a HEK293 specific HCP ELISA FIG. 3 describes the principle of plotting results (calculated concentrations) obtained from the CAR assay vs. calculated concentrations obtained from the FX assay. Samples (encircled) containing expected amount of both hexon (FX assay) and fiber (CAR assay) are assumed to be functional infectious virus particles. In contrast, samples containing large amounts of fiber, but low level of hexons would be discarded as non functional. The same applies for samples containing large amounts of hexon but low level of fiber, they would be discarded as being non infectious virus particles. The virus titer as well as quality can be followed by response and response ratio, across the different steps in a production process, including cell culture and infection, cell lysis to release virus, filtrations and purification steps to finally obtain a pure and functional virus for research or clinical studies or clinical use. Usually, the titer and quality is monitored by a whole set of different analysis methods. This method can by the same method simultaneously analyze total and infectious virus titer.

The invention will now be described more closely in association with some non-limiting Examples.

Materials and Methods

Biacore T200, Series S Sensor Chip CM5, HBS-P+ buffer, HBS-EP+ buffer, Amine Coupling Kit and Ad5 virus samples were from GE Healthcare. Factor X was from Haematologic Technologies, CAR (recombinant human Coxsackie Adenovirus receptor) was from Abcam and ATCC (American Type Culture Collection) standard, containing $5.8 \cdot 0.10^{11}$ Ad5 particles/ml, was from LGC Standards GmbH.

Example 1: Assay with Standard Curve, CAR Immobilised

An assay based on CAR, using a standard curve, was developed.

CAR Immobilisation, CM5 Chip

HBS-EP+ was used as running buffer. CAR was immobilized to a CM5 sensor chip using an Amine Coupling Kit according to the manufacturer's instructions. Briefly, after activation of the chip CAR (12.5 ug/ml in 10 mM Na-acetate, pH 5.5), was injected during 10 min followed by deactivation of remaining activated sites on the chip. Approximately 2000 RU CAR was covalently immobilized using those conditions.

Assay Parameters

Running buffer and sample buffer was HBS-EP+.

400 s sample injection time at 5 ul/min was used followed by regeneration of the surface using two 30 s injections of 10 mM glycine, pH 1.5 and last a 60 s stabilisation time.

Standard curve range: The standard curve range was selected to obtain robust response levels and at the same time being able to dilute samples as far as possible.

Run order: Both standard points and sample dilutions were run in order from low to high concentration.

Reference flow cell: No reference flow cell was used in accordance with our recommendations for concentration determination with standard curve.

Non specific binding: Non specific binding towards the dextran was checked using negative control samples (not shown) and found insignificant.

Assay Performance

Figure 4:
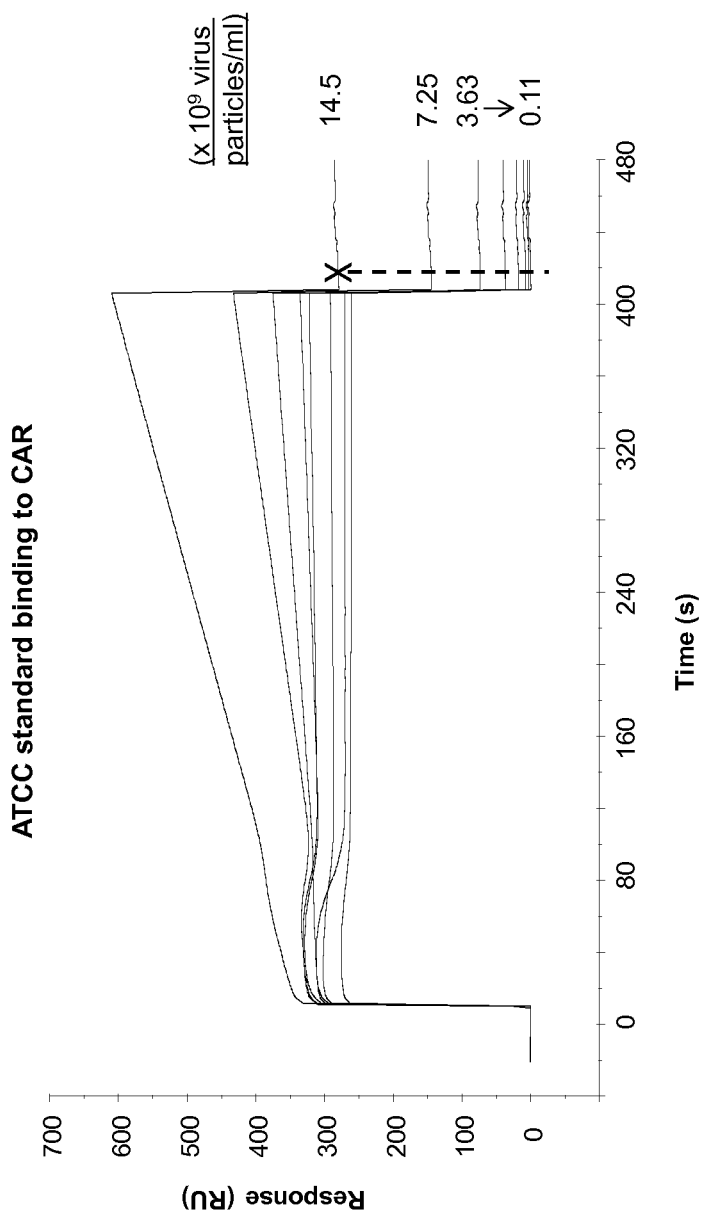
FIG. 4 is an overlay plot of sensorgrams from different concentrations of adenovirus binding to immobilized CAR.

FIG. 4 is an example showing sensorgrams from two series of ATCC (American Type Culture Collection) standard points (0.11, 0.23, 0.46, 0.91, 1.82, 3.63, 7.25 and 14.5e9 Ad5 particles/ml) run before and after a total of 14 sample injections (samples diluted 100 and 200 times). Responses were taken at the "Stability early" report point (marked as X) and used to construct the standard curve.

The CV (coefficient of variation) was calculated on different dilutions of the same adenovirus process sample and was for most samples below 10%, demonstrating that the two different dilutions both result in similar concentration estimates.

Repeated testing of samples both on the same sensor chip and on new immobilized sensor chip shows low inter assay variation.

The CAR immobilized surface is stable for at least a week depending of the number and condition of the samples.

Results

Figure 5:
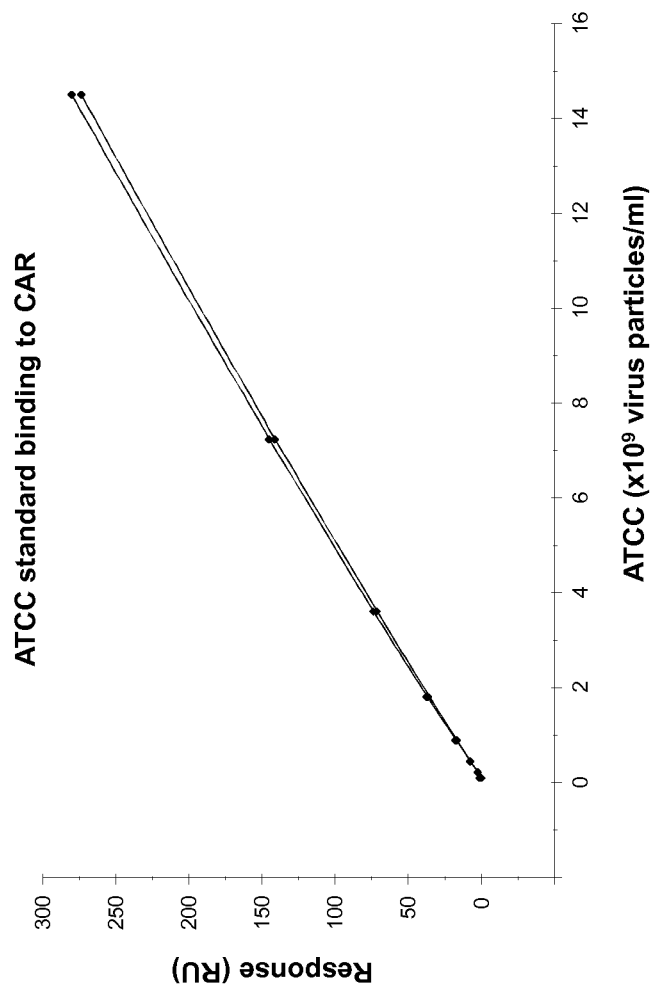
FIG. 5 is a dose-response curve of injected adenovirus in different concentrations against response units (RU)

FIG. 5 shows the resulting standard curves obtained from the FIG. 3 ATCC standard injections. A linear relationship between virus concentration and response was obtained. The two standard curves are almost overlapping demonstrating that the assay is optimised to give similar results in the beginning as well as after samples were tested.

Example 2: Assay with Standard Curve, FX Immobilised

An assay based on FX, using a standard curve, was developed in parallel with the CAR based assay. The aim being that the FX assay could be used as a complement to the CAR based assay to obtain quantitation based on binding to virus hexon.

FX Immobilisation, CM5 Chip

HBS-P+, 5 mM $CaCl_2$ was used as running buffer. FX was immobilized to a CM5 sensorchip using an Amine Coupling Kit according to the manufacturer's instructions. Briefly, after activation of the chip FX (15 ug/ml in 10 mM Na-acetate, pH 5.0), was injected during 20 min followed by deactivation of remaining activated sites on the chip. About 4500 RU FX was covalently immobilized using those conditions.

Assay Parameters and Assay Performance

The same sample injection parameters as for the CAR based assay were selected, except for running buffer and sample buffer which was HBS-P+, 5 mM $CaCl_2$), and the regeneration solution which was HBS-EP+, injected during 60 s, breaking the $Ca^{2+}$ dependent binding of Ad5 to FX.

Results

FIG. 6 shows injection of ATCC standard binding to FX. ATCC standards were injected in the following order: first one complete calibration curve, injected from low to high concentration, then the next standard curve. Standard point range was from 0.9e8 to 2.9e9 virus particles/ml. Responses were taken at the "Stability early" report point (marked as X) and used to construct the standard curve.

Figure 7:
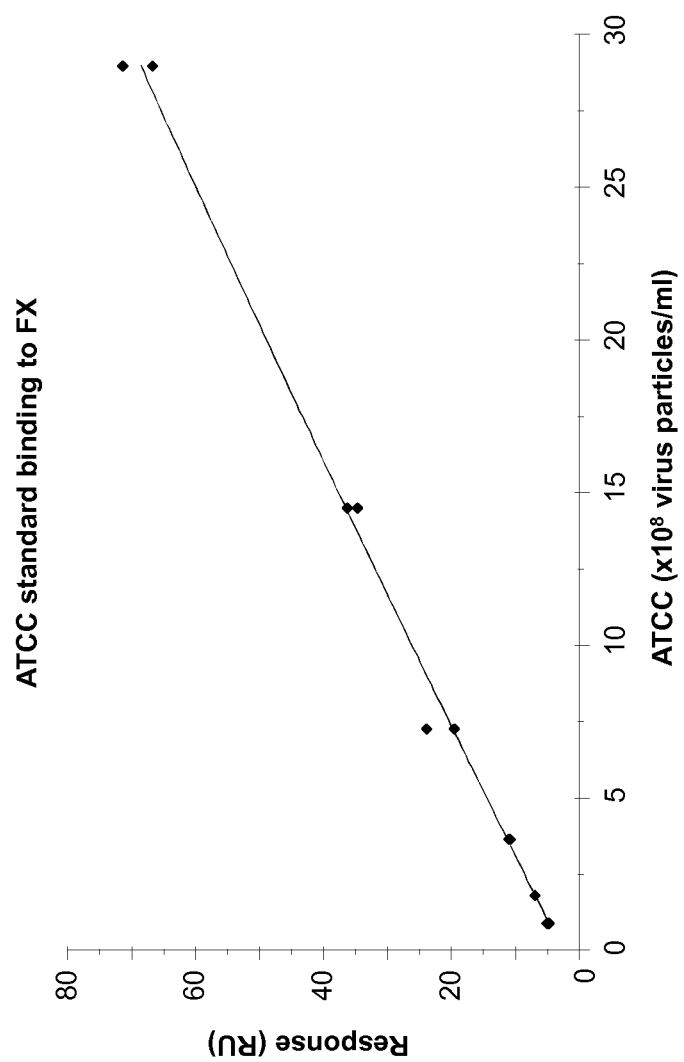
FIG. 7 is a dose-response curve of injected adenovirus in different concentrations against response units (RU)

FIG. 7 shows a calibration curve from FIG. 5 data, that is 0.9e8 to 2.9e9 virus particles/ml. A linear relationship between virus concentration and response was obtained. The fitted standard curve is in this example based on the mean of two separate concentration series, also demonstrating that the assay is optimised to give similar results for repeated standard curves.

Example 3: Sandwich Assay with CAR and Factor X

This Example relates to a sandwich assay for check of virus integrity. In a first step, the adenovirus particles bind via the fiber knob to the coxsackievirus and adenovirus receptor (CAR) immobilized on a SPR sensor chip. Human blood coagulation factor X (FX) binding to hexon protein is then injected and level of binding to the virus indicates the level of intact virus particles.

Figure 8:
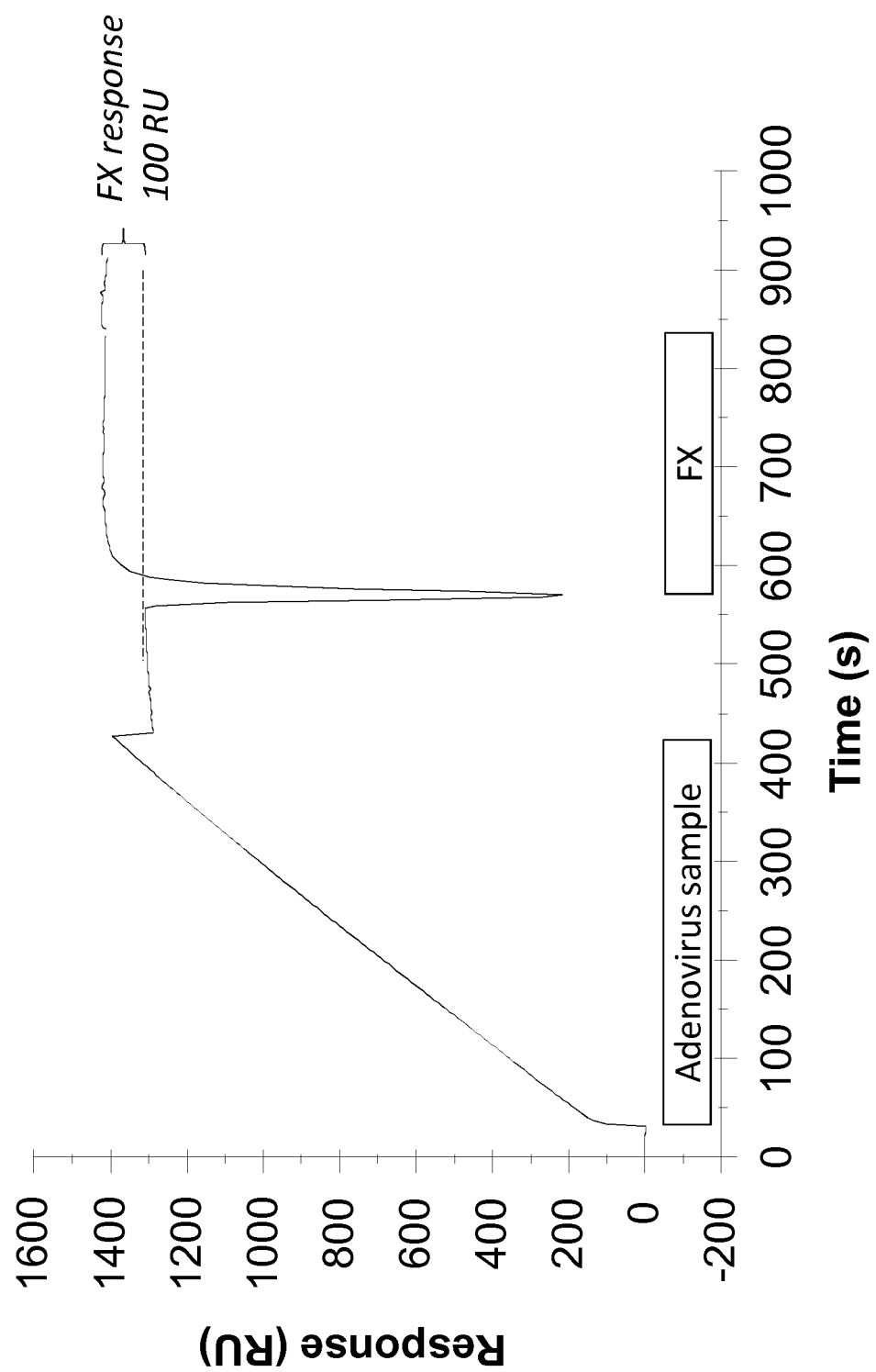
FIG. 8 is a sensorgram of a virus sample injected first and binding to immobilized CAR, and followed by an injection of FX binding to the virus sample.

This Example is described more closely in FIG. 8. CAR was immobilized to a CM5 sensor chip using an Amine Coupling Kit according to the manufacturer's instructions.

A virus sample was injected and allowed to bind to the CAR surface. This was followed by a second injection using FX. HBS-P+, 5 mM $CaCl_2$ was used as running buffer and sample buffer. The sample was injected for 400 s at 5 ul/min followed by injection of FX for 300 s at 5 ul/min. Finally regeneration of the surface using two 30 s injections of 10 mM glycine, pH 1.5 and last a 60 s stabilisation time. In this way, the concentration of intact adenovirus particles can be confirmed.

Example 4: CFCA Assay, CAR Immobilised, CM5 Chip

This Example relates to a CFCA (Calibration free concentration assay) which differs from the above Examples in that the concentration is determined without a standard curve.

Prior to the CFCA assay the following parameters were established:
- CAR was immobilised as described previously in Example 1.
- MW of adenovirus: 1.57e8 Da
- Diffusion coefficient for adenovirus: 5.01e-12
- The same regeneration conditions as for the CAR standard curve assay were used.

ATCC standard was diluted ×100 (to (9.3e-12 M) and injected over the CAR surface, using flow rates 3 and 100 ul/min, see FIG. 8.

Figure 9:
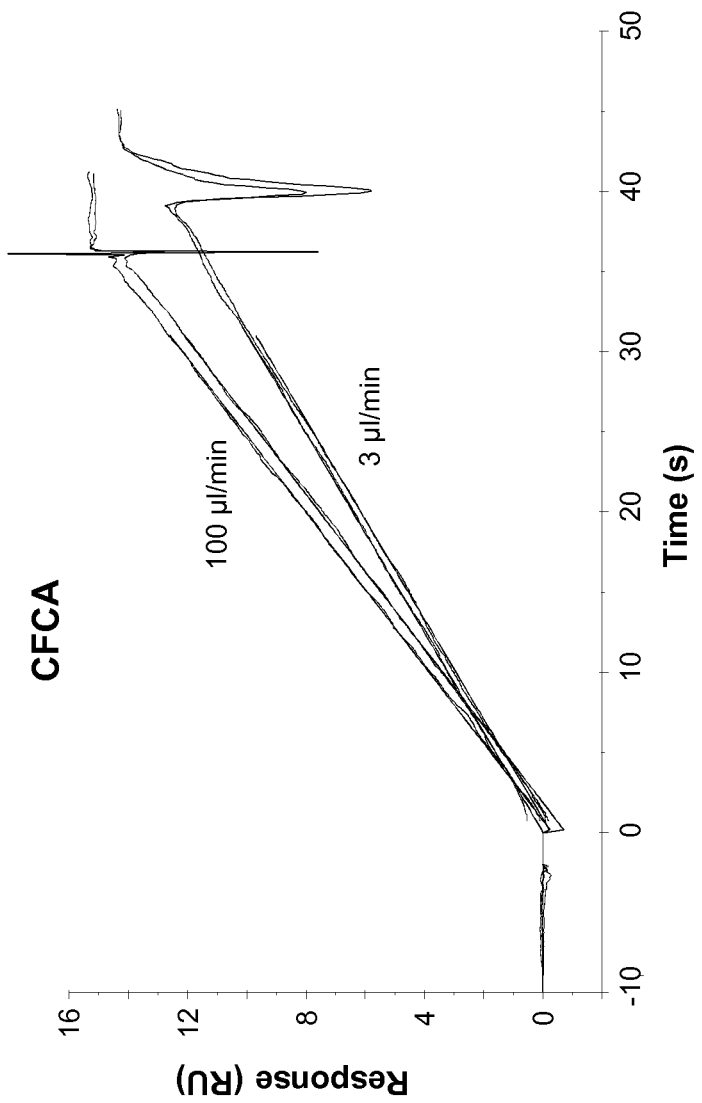
FIG. 9 shows the result of a CFCA assay with immobilized CAR.

FIG. 9 shows CFCA evaluation with 3 and 100 ul/min injections for ATCC diluted ×100 (9.3e-12 M). Duplicate injections were fitted using the CFCA software and concentrations were calculated.

Results
- Vial conc: 9.3e-10 M (5.8e11 particles/ml)
- CFCA calc conc: 5.1e-10 M
- QC ratio=0.13

Obtained calculated concentrations were in the right range, a little over half of what was stated on the vial from the manufacturer. The ATCC manufacturer states >70% single particles, the rest doublets, triplets or multiplets.

The invention claimed is:

1. A method for determining adenovirus concentration in a sample, comprising subjecting said sample to surface plasmon resonance (SPR) assay with immobilized Factor X (FX) and/or immobilized coxsackievirus and adenovirus receptor (CAR) on a sensor surface configured to determine the adenovirus concentration, wherein the adenovirus concentration is determined from sample binding to immobilized FX and/or immobilized CAR.

2. The method according to claim 1, wherein FX or CAR are immobilized.

3. The method according to claim 1, wherein said FX and said CAR are immobilized on different SPR surfaces or on the same SPR surface but on different regions or areas thereof.

4. The method according to claim 1, wherein functional adenovirus is determined by binding to both FX and CAR by the same adenovirus.

5. The method according to claim 1, wherein FX or CAR is immobilized and the one of FX and CAR that is not immobilized is injected in a second step of the SPR assay for binding to relevant parts of the sample (adenovirus) already bound to the surface in a sandwich assay.

6. The method according to claim 1, wherein CAR is replaced by a ligand binding to adenovirus fiber.

7. The method according to claim 1, wherein FX is replaced by a ligand binding to adenovirus hexon.

8. The method according to claim 1, wherein the ratio between functional (active) adenovirus concentration and total adenovirus concentration is determined.

9. The method according to claim 1, wherein the result from the SPR assay(s) are determined with standard curves.

10. The method according to claim 1, wherein the SPR assay(s) is/are calibration free concentration analysis (CFCA) assays.

11. The method of claim 1, wherein the adenovirus concentration is used for quality control in an adenovirus purification process.

12. The method of claim 1, wherein the adenovirus concentration is used for quality control in a purification process of adenovirus for gene therapy.

13. The method according to claim 6, wherein the ligand binding to adenovirus fiber is an anti-adenovirus fiber antibody.

14. The method according to claim 7, wherein the ligand binding to adenovirus hexon is an anti-adenovirus hexon antibody.

* * * * *